(12) United States Patent
Sundaramurthi (10) Patent No.: US 11,911,500 B2
(45) Date of Patent: *Feb. 27, 2024

(54) MEDROXYPROGESTERONE ACETATE INJECTABLE COMPOSITIONS AND METHODS OF USE

(71) Applicant: Family Health International, Durham, NC (US)

(72) Inventor: Prakash Sundaramurthi, Fort Washington, PA (US)

(73) Assignee: Family Health International, Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 17/489,982

(22) Filed: Sep. 30, 2021

(65) Prior Publication Data

US 2022/0047500 A1 Feb. 17, 2022

Related U.S. Application Data

(62) Division of application No. 16/081,068, filed as application No. PCT/IB2017/051225 on Mar. 2, 2017, now Pat. No. 11,135,154.

(60) Provisional application No. 62/302,290, filed on Mar. 2, 2016.

(51) Int. Cl.
| | | |
|---|---|---|
| A61K 31/57 | (2006.01) | |
| A61K 9/00 | (2006.01) | |
| A61K 47/10 | (2017.01) | |
| A61K 47/20 | (2006.01) | |
| A61K 9/10 | (2006.01) | |
| A61K 47/18 | (2017.01) | |
| A61K 31/225 | (2006.01) | |
| A61P 29/02 | (2006.01) | |
| A61P 15/18 | (2006.01) | |
| A61P 35/00 | (2006.01) | |
| A61K 47/02 | (2006.01) | |
| A61K 47/14 | (2017.01) | |

(52) U.S. Cl.
CPC .............. *A61K 9/0019* (2013.01); *A61K 9/10* (2013.01); *A61K 31/225* (2013.01); *A61K 31/57* (2013.01); *A61K 47/02* (2013.01); *A61K 47/10* (2013.01); *A61K 47/14* (2013.01); *A61K 47/183* (2013.01); *A61K 47/20* (2013.01); *A61P 15/18* (2018.01); *A61P 29/02* (2018.01); *A61P 35/00* (2018.01)

(58) Field of Classification Search
None
See application file for complete search history.

(56) References Cited

U.S. PATENT DOCUMENTS

| 11,135,154 B2 * | 10/2021 | Sundaramurthi ...... A61K 47/14 |
| 2004/0039366 A1 | 2/2004 | MacLeod |
| 2009/0004262 A1 | 1/2009 | Shaw et al. |
| 2013/0183383 A1 | 7/2013 | Phang et al. |

FOREIGN PATENT DOCUMENTS

| WO | 01/87266 A1 | 11/2001 |
| WO | 2004/018312 A1 | 3/2004 |
| WO | 2017/149492 A1 | 9/2017 |

OTHER PUBLICATIONS

Anonymous: "depo-subQ provera 104 medroxyprogesterone acetate injectable suspension 104 mg/0.65 ml", Jan. 1, 2015 (Jan. 1, 2015), XP55374545, Retrieved from the Internet: URL:https://dailymed.nlm.nih.gov/dailymed/archives/fdaDrugInfo.cfm?archiveid=168634 [retrieved on May 19, 2017].

Docusate Sodium, A pharmaceutical Guide of Excipients, https://www.pharmaexcipients.com/news/docusate-sodium-a-pharmaceutical-grade-excipient/, 2017 (Year: 2017).

* cited by examiner

*Primary Examiner* — Jake M Vu
(74) *Attorney, Agent, or Firm* — Parker Highlander PLLC (57) ABSTRACT

The disclosure is directed to medroxyprogesterone compositions suitable for subcutaneous injection comprising about 360 mg/ml to 440 mg/ml medroxyprogesterone acetate, 1.35 mg/ml to 1.65 mg/ml docusate sodium, polyethylene glycol, and water. Methods of using these compositions are also described.

20 Claims, 2 Drawing Sheets

MEDROXYPROGESTERONE ACETATE INJECTABLE COMPOSITIONS AND METHODS OF USE

CROSS REFERENCE TO RELATED APPLICATION

This application is a divisional of U.S. application Ser. No. 16/081,068, filed Aug. 30, 2018, which is the National Stage Application of International Patent Application No. PCT/IB2017/051225, filed Mar. 2, 2017, which claims the benefit of U.S. Application No. 62/302,290, filed Mar. 2, 2016, the entireties of which are incorporated herein by reference.

TECHNICAL FIELD

The disclosure is directed to medroxyprogesterone acetate compositions suitable for subcutaneous injection.

BACKGROUND

Medroxyprogesterone acetate has been approved in the United States for prevention of pregnancy in women of childbearing potential as well as for the management of endometriosis-associated pain. One such product, Depo-SubQ Provera 104® (medroxyprogesterone acetate injectable suspension) is provided as a single subcutaneous injection of 104 mg once every 12 to 14 weeks. The relatively short duration of action of this product requires four or more medical visits each year, which can impede patient compliance with the treatment protocol.

There is a need for a new formulation of medroxyprogesterone acetate with a longer duration of action that will allow for fewer yearly medical visits.

SUMMARY

The present disclosure is directed to compositions for subcutaneous injection comprising medroxyprogesterone acetate at a concentration of about 360 mg/ml to 440 mg/ml, docusate sodium at a concentration of about 1.35 mg/ml to 1.65 mg/ml, polyethylene glycol, and water. Methods of using the compositions are also described.

DETAILED DESCRIPTION OF ILLUSTRATIVE EMBODIMENTS

The present disclosure may be understood more readily by reference to the following detailed description taken in connection with the accompanying figures and examples, which form a part of this disclosure. It is to be understood that this disclosure is not limited to the specific compositions or methods described and/or shown herein, and that the terminology used herein is for the purpose of describing particular embodiments by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. All ranges are inclusive and combinable.

A. General

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9 to 1.1.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination. Further, reference to values stated in ranges includes each and every value within that range.

As used herein, the term "composition" shall mean a composition that is made under conditions such that it is suitable for administration to humans, e.g., it is made under GMP conditions and contains pharmaceutically acceptable excipients, e.g., without limitation, stabilizers, bulking agents, buffers, carriers, diluents, vehicles, solubilizers, and binders. As used herein pharmaceutical composition includes, but is not limited to, a liquid form ready for subcutaneous injection or infusion.

The compositions described herein comprise any one or more active pharmaceutical compounds. These active pharmaceutical compounds can include, for example, any agent for which extended release is desired. Such active pharmaceutical compounds can be used for the treatment of infectious diseases, cancer, psychiatric disorders, uterine disorders, and hormonal disorders, as well as for the prevention of pregnancy.

In preferred aspects, the compositions described herein comprise active pharmaceutical ingredients known in the art to be useful for preventing pregnancy or for treating endometriosis-associated pain, renal carcinoma, or endometrial carcinoma in a female patient. The active pharmaceutical ingredient may be selected by one skilled in the art depending on the condition being treated. Selection of the active pharmaceutical ingredient may also depend on other factors including, without limitation, components of the composition, mode of delivery, severity of the condition being treated, the patient's age and weight, and any other active ingredients used in the composition. The compositions may contain one active pharmaceutical ingredient, two active pharmaceutical ingredients, or three or more active pharmaceutical ingredients. For example, the active pharmaceutical ingredient may be estrogen such as ethinyl estradiol or a progestin such as norethindrone, levonorgestrel, desogestrel, ethynidiol diacetate, norgestimate, norenthindrone acetate, norgestrel, drospirenone, norelgestromin or medroxyprogesterone acetate.

In other preferred aspects, the compositions described herein for subcutaneous injection comprise medroxyprogesterone acetate. Medroxyprogesterone acetate may also be referred to by one of skill in the art as 6α-6-methyl-3,20-dioxopregna-4-en-17-yl acetate, Pregna-4-ene-3,20-dione, 17-(acetyloxy)-6-methyl,6(α), or 17 alpha-hydroxy-6(α)-methylpregn-4-ene 3,20-dione acetate. Concentrations of medroxyprogesterone acetate in the compositions can range from about 360 mg/ml to 440 mg/ml. For example, the concentrations can comprise about 360, 365, 370, 375, 380, 385, 390, 395, 400, 405, 410, 415, 420, 425, 430, 435 or about 440 mg/ml. In other aspects, the concentration of medroxyprogesterone acetate in the compositions can range from about 150 mg/ml to 440 mg/ml or from about 150 mg/mL to about 360 mg/mL. For example, the concentrations can comprise about 150, 160, 170, 180, 190, 200, 210, 220, 230, 240, 250, 260, 270, 280, 290, 300, 310, 320, 330, 340, 350, or about 360 mg/mL.

The compositions of the disclosure further comprise docusate sodium. As used herein, "docusate sodium" refers to the excipient with the molecular formula $C_{20}H_{37}NaO_7S$, and may also be referred to by one of skill in the art as dioctyl sodium sulfosuccinate or DSS. The compositions of the disclosure may comprise any amount of docusate sodium. Preferably, concentrations of docusate sodium can range from about 0.1 mg/ml to about 3.0 mg/ml. For example, the concentrations can comprise about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0 mg/ml. More preferably, concentrations of docusate sodium can range from about 1.35 mg/ml to about 1.65 mg/ml. For example, the concentrations can comprise about 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64 or about 1.65 mg/ml.

The compositions of the disclosure further comprise polyethylene glycol. Polyethylene glycol, or PEG, is a polyether compound that may also be referred to by one of skill in the art as polyethylene oxide or polyoxyethylene, depending on its molecular weight. In preferred embodiments, polyethylene glycol has an average molecular weight of between about 3,000 and about 3,700 g/mol. Most preferably, polyethylene glycol has an average molecular weight of about 3,350 g/mol. Concentrations of polyethylene glycol in the compositions of the disclosure preferably range from about 18 mg/ml to about 23 mg/ml. For example, the concentrations may be about 18, 19, 20, 21, 22, or 23 mg/ml. In other aspects, concentrations of polyethylene glycol in the compositions of the disclosure range from about 5 mg/ml to about 50 mg/ml. For example, the concentrations may be about 5, 10, 15, 20, 25, 30, 35, 40, 45, or about 50 mg/ml.

The compositions of the disclosure also include water. The water used in the compositions is preferably sterile water for injection.

In some embodiments of the disclosure, the compositions may further comprise tonicity adjusters such as sulfate salts or sodium salts. Sulfate salts include, for example, sodium sulfate (e.g., sodium sulfate anhydrous) or magnesium sulfate (e.g., magnesium sulfate heptahydrate), as well as combinations thereof. Sodium salts include, for example, sodium chloride.

In some embodiments of the disclosure, the compositions may further comprise a stabilizer. As used herein, "stabilizer" refers to a stabilizing compound or combination of stabilizing compounds which maintain the pH of the composition. Examples of stabilizers that may be useful in the present compositions include, without limitation, thioglycerol, monothioglycerol, lipoic acid, propyl gallate, cysteine, sodium formaldehyde sulfoxylate, or dihydrolipoic acid, and methionine (e.g., L-methionine), as well as combinations thereof. Preferred stabilizers include, without limitation, monothioglycerol, cysteine, sodium formaldehyde sulfoxylate, or methionine. An exemplary stabilizer is methionine.

In some embodiments of the disclosure, the compositions may further comprise buffering salts. Examples of buffering salts that may be useful in the present compositions include phosphate salts, acetate salts, citrate salts, tartrate salts, lactate salts, succinate salts, maleate salts, and histidine salts, as known in the art. In preferred embodiments, the buffering salt is a phosphate salt including, for example, monobasic sodium phosphate, dibasic sodium phosphate, or a combination thereof.

In preferred aspects of the disclosure, the compositions further comprise sodium sulfate, methionine, monobasic sodium phosphate, and dibasic sodium phosphate. Exemplary compositions of the disclosure comprise medroxyprogesterone acetate, docusate sodium, polyethylene glycol, water, sodium sulfate, methionine, monobasic sodium phosphate, and dibasic sodium phosphate.

In addition to the medroxyprogesterone acetate and foregoing ingredients, the compositions of the disclosure may comprise one or more additional pharmaceutically acceptable excipients. "Excipient" means the substances used to formulate active pharmaceutical ingredients (API) into pharmaceutical formulations; in a preferred embodiment, an excipient does not lower or interfere with the primary therapeutic effect of the API. Preferably, an excipient is therapeutically inert. The term "excipient" encompasses carriers, diluents, vehicles, solubilizers, stabilizers, bulking agents, and binders. Excipients can also be those substances present in a pharmaceutical formulation as an indirect or unintended result of the manufacturing process. Preferably, excipients are approved for or considered to be safe for human and animal administration, i.e., GRAS substances (generally regarded as safe). GRAS substances are listed by the Food and Drug administration in the Code of Federal Regulations (CFR) at 21 CFR § 182 and 21 CFR § 184, incorporated herein by reference.

The excipients can be included in the compositions described herein and in the final dosage forms described herein. One would be able to select one or more suitable excipients using skill in the art and the teachings herein. In some embodiments, the excipients may be selected from those described in Handbook of Pharmaceutical Excipients, 5th ed. (2006). In preferred embodiments, the excipient includes, without limitation, one or more of a suspending agent, surfactant, tonicity adjuster, stabilizer, buffer, vehicle, or a combination thereof.

In some aspects of the disclosure, the pH of the composition is about 4.0 to about 7.0. In some embodiments of the disclosure, the pH of the composition is about 6.0 to about 7.0. For example, the pH of the composition is about 4.0, 4.5, 5.0, 5.5, 6.0, 6.5, or about 7.0. In preferred embodiments, the pH of the composition is about 6.6 to about 6.7. It is advantageous for the pH of the composition to not decrease during storage so that the composition may be safely administered to patients without generating significant pain.

B. Dosage Forms

Suitable dosage forms include, but are not limited to oral, rectal, sub-lingual, mucosal, nasal, ophthalmic, subcutaneous, intramuscular, intravenous, transdermal, spinal, intrathecal, intraarticular, intra-arterial, sub-arachnoid, bronchial, lymphatic, and intra-uterine administration, and other dosage forms for systemic delivery of active ingredients. In a preferred embodiment, the dosage form is suitable for subcutaneous injection. The compositions may be administered with a syringe-needle suitable for subcutaneous use. As used herein, the term "subcutaneous" means under the skin, and is understood by those of skill in the art to be interchangeable with the term subdermal.

Compositions of the disclosure can be provided a single unit dosage forms. A "single unit dose" as used herein means the pharmaceutical compositions disclosed herein being in a container and in an amount suitable for reconstitution and/or administration of a single dose, wherein the amount suitable for reconstitution and administration of a single dose is a therapeutically effective amount. The single unit dose, although typically in the form of a vial, may be any suitable container, such as ampoules, syringes (e.g., pre-filled syringes), co-vials, cartridges, which are capable of maintaining a sterile environment. Such containers can be glass or plastic, provided that the material does not act with the medroxyprogesterone acetate compositions. The closure is typically a stopper, most typically a sterile rubber stopper, which affords a hermetic seal. In preferred embodiments, the composition is supplied as a white suspension packed in a 3 mL United States Pharmacopeia (USP) Type 1 clear glass borosilicate vial closed with a 13 mm chlorobutyl siliconized rubber stopper and aluminum cap, fitted with an orange color flip-off disk. In preferred embodiments, the vial is filled with about 1.18 mL to about 1.34 mL of the compositions. For example, the volume of compositions can comprise about 1.18, 1.19, 1.20, 1.21, 1.22, 1.23, 1.24, 1.25, 1.26, 1.27, 1.28, 1.29, 1.30, 1.31, 1.32, 1.33 or 1.34 mL. Preferably, the volume of the composition is about 1.26 mL. In all cases, the ultimate dosage form should be sterile, fluid and stable under the conditions of manufacture and storage.

As used herein, the term "vial" refers to any walled container, whether rigid or flexible.

"Therapeutically effective amount" refers to an amount of an active pharmaceutical agent described herein which is sufficient to inhibit, halt, or cause an improvement in a disorder or condition being treated in a particular subject or subject population. In certain embodiments, in a human or other mammal, a therapeutically effective amount can be determined experimentally in a laboratory or clinical setting, or may be the amount required by government guidelines for the particular disease and subject being treated. It should be appreciated that determination of proper dosage forms, dosage amounts, and routes of administration is within the level of ordinary skill in the pharmaceutical and medical arts.

C. Treatment Methods

The compositions described herein may be employed in methods for preventing pregnancy. The compositions described herein can also be used for treating endometriosis-associated pain. In other aspects, the compositions can be used to treat renal carcinoma. In still other aspects, the compositions can be used to treat endometrial carcinoma. As used herein, "patient" or "subject" is intended to mean a mammal. Thus, the compositions described herein are applicable to human and nonhuman subjects. In certain embodiments, the compositions described herein are applicable to humans. In some embodiments, the patient is a female.

"Treatment" refers to the acute or prophylactic diminishment or alleviation of at least one symptom or characteristic associated or caused by a disorder being treated. In certain embodiments, treatment can include diminishment of several symptoms of a disorder or complete eradication of a disorder.

As used herein, "preventing pregnancy" refers to the suppression of ovulation in women of childbearing potential, where ovulation is defined as a single elevated serum progesterone level. In preferred embodiments, an increase in progesterone of 3 to 5 ng/mL sustained over at least 5 days indicates ovulation.

"Endometriosis-associated pain" as used herein refers to the pain caused when the tissue lining the inside of the uterus (the endometrium) grows outside of the uterus.

"Renal carcinoma" refers to a cancer that originates in the kidney, commonly originating in the lining of the renal tubules. "Endometrial carcinoma" refers to a cancer that originates in the uterus, specifically originating in the endometrial cells forming the lining of the uterus.

Accordingly, the methods of using the compositions described herein have a wide-sweeping use in the treatment of a variety of indications. The use of the compositions does not depend on the method of use. In some embodiments, the disorder or condition being treated is acute, chronic, or a combination thereof.

The methods include administering to the patient the compositions described herein. The methods may also include identifying a patient in need of treatment with medroxyprogesterone acetate. Determination of the proper dosage of the active pharmaceutical agent discussed herein for a particular situation is within the skill of the practitioner.

D. Stability

The invention provides stable, pharmaceutically acceptable compositions comprising medroxyprogesterone acetate. In particular, the disclosure provides compositions which may be administered about once every four months, about once every five months or about once every six months. An aspect of the disclosure is conditions and means for enhancing the stability of the medroxyprogesterone acetate composition upon shelf storage and/or upon reconstitution.

"Stable pharmaceutical composition" refers to any pharmaceutical composition having sufficient stability to have utility as a pharmaceutical product. Preferably, a stable pharmaceutical composition has sufficient stability to allow storage at a convenient temperature, preferably between −20° C. and 40° C., more preferably about 2° C. to about 30° C., for a reasonable period of time, e.g., the shelf-life of the product which can be as short as one month but is typically six months or longer, more preferably one year or longer even more preferably twenty-four months or longer, and even more preferably thirty-six months or longer. The shelf-life or expiration can be that amount of time where the active ingredient degrades to a point below 90% purity. For purposes of the present invention stable pharmaceutical composition includes reference to pharmaceutical compositions with specific ranges of impurities as described herein. Preferably, a stable pharmaceutical composition is one which has minimal degradation of the active ingredient, e.g., it retains at least about 85% of un-degraded active, preferably at least about 90%, and more preferably at least about 95%, after storage at 2-30° C. for a 2-3 year period of time.

"Degraded" as used herein means that the active ingredient has undergone a change in chemical structure.

"Controlling" as used herein means putting process controls in place to facilitate achievement of the thing being controlled. For example, in a given case, "controlling" can mean testing samples of each lot or a number of lots regularly or randomly or selecting process conditions so as to facilitate regulatory approval of a pharmaceutical product by a regulatory agency, such as the U.S. Food and Drug Administration and similar agencies in other countries or regions.

The term "pharmaceutically acceptable" as used herein means that the thing that is pharmaceutically acceptable, e.g., components, including containers, of a pharmaceutical composition, does not cause unacceptable loss of pharmacological activity or unacceptable adverse side effects.

Examples of pharmaceutically acceptable components are provided in The United States Pharmacopeia (USP), The National Formulary (NF), adopted at the United States Pharmacopeial Convention, held in Rockville, Md. in 1990 and FDA Inactive Ingredient Guide 1990, 1996 issued by the U.S. Food and Drug Administration (both are hereby incorporated by reference herein, including any drawings). Other grades of solutions or components that meet necessary limits and/or specifications that are outside of the USP/NF may also be used.

As used herein, "storage condition" refers to the number of months the compositions are stored at a given temperature with a given humidity in either an upright (U) or inverted (I) position. In some embodiments of the disclosure, the compositions may be stored from a range of 0 to 6 months. For example, compositions may be stored for about 0, 1, 2, 3, 4, 5, or about 6 months. In some embodiments of the disclosure, the composition may be stored at a range of temperatures from about 25 to about 60° C. For example, the compositions may be stored at about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or about 60° C. In some embodiments, the compositions may be stored at a range of humidity percentages from about 60 to about 75 percent humidity. For example, the compositions may be stored at about 60, 61, 62, 63, 64, 65, 66, 67, 68, 69, 70, 71, 72, 73, 74 or about 75 percent humidity. In some embodiments of the disclosure, the compositions are stable when stored upright or inverted.

As used herein, "PSD" refers to particle-size distribution of particles in a fluid. Dx(N) refers to the mathematical function wherein N represents the average particle diameter by mass. For example, Dx(10) is the diameter at which 10% of the sample's mass is comprised of particles with a diameter less than this value. Dx(50) is the diameter at which 50% of the sample's mass is comprised of particles with a diameter less than this value. Dx(90) is the diameter at which 90% of the sample's mass is comprised of particles with a diameter less than this value.

As used herein, "impurities" means the impurities in the composition as measured by high performance liquid chromatography (HPLC) as compared to a reference or control. Impurities may include, for example, acetoxyprogesterone, medroxyprogesterone, megestrol acetate, 6β-Methyl-acetoxyprogestrone or acetoxyprogesterone-6-methylene.

As used herein, "resuspendability" means dispersing the composition by shaking and comparing to the description of the product. If the appearance matches the description with no signs of caking or agglomerated particles, it conforms. Compositions of the disclosure are resuspendable after about 20 seconds to about 300 seconds. In some aspects, compositions of the disclosure are resuspendable after about 20 seconds to about 200 seconds. For example, compositions can be resuspended after about 20, 30, 40, 50, 60, 70, 80, 90, 100, 110, 120, 130, 140, 150, 160, 170, 180, 190, or about 200 seconds. In other aspects, compositions can be resuspended after about 210, 220, 230, 240, 250, 260, 270, 280, 290, or about 300 seconds.

As used herein, "syringeability" is determined by withdrawing the composition using a common syringe and needle type used for the administration of the pharmaceutically acceptable composition and dispensing the solution, during which time, no clogs are observed in the syringe or the needle. Preferably, a syringe with a 23 gauge, ⅜ inch safety needle is used to test syringeability. Compositions of the disclosure are syringeable, especially after resuspension by shaking.

The following examples are offered for illustrative purposes, and are not intended to limit the invention in any manner. Those of skill in the art will readily recognize a variety of noncritical parameters which can be changed or modified to yield essentially the same results.

EXAMPLES

Example 1: Medroxyprogesterone Acetate Compositions

The quantitative composition and function of each component in an exemplary embodiment of the disclosure is provided in Table 1.

TABLE 1

Unit composition in medroxyprogesterone acetate compositions

| Ingredients | Function of Components | Concentration (mg/mL) | Content (mg/vial) |
| --- | --- | --- | --- |
| Medroxyprogesterone Acetate, USP | Active Pharmaceutical Ingredient | 400 | 504 |
| Polyethylene glycol, 3350 USP/NF | Suspending Agent | 20.3 | 25.59 |
| Docusate sodium, USP/EP | Surfactant | 1.5 | 1.89 |
| Sodium sulfate anhydrous, USP/BP/Eur | Tonicity Adjuster | 11 | 13.86 |
| L-Methionine, USP/EP/JP | Stabilizer | 1.5 | 1.89 |
| Monobasic sodium phosphate, USP | Buffer | 0.25 | 0.32 |
| Dibasic Sodium phosphate, USP | Buffer | 0.52 | 0.66 |
| Water for Injection, USP | Vehicle | Q.S to 1 mL~1.07 g | Q.S to 1.26 mL |

Example 2: IID-Conforming Excipient Levels

All excipients except docusate sodium and sodium sulfate anhydrous fall below the inactive ingredient database (IID) limits for the subcutaneous route of administration as supplied in the FDA IID database. IID limits for docusate sodium and sodium sulfate anhydrous are not available in FDA IID database. Separate non-clinical studies were performed to qualify these excipients for the subcutaneous route of administration.

TABLE 2

IID levels of the excipients used in the medroxyprogesterone acetate compositions

| Ingredients | IID Levels (%) (IM/SC Route of Administration) | Concentration (mg/mL) | % w/v |
|---|---|---|---|
| Polyethylene glycol, 3350 USP/NF | 2.88 | 20.3 | 2.03 |
| Docusate sodium, USP/EP | 0.015/NA | 1.5 | 0.15 |
| Sodium sulfate anhydrous, USP/BP/Eur | NA | 11 | 1.10 |
| L-Methionine, USP/EP/JP | 0.15 | 1.5 | 0.15 |
| Monobasic sodium phosphate, USP | 0.06 | 0.25 | 0.025 |
| Dibasic Sodium phosphate, USP | 0.07 | 0.52 | 0.052 |
| Sodium chloride | 1.23 for SC route 0.9 for IM/SC route | 4.5 | 0.45 |
| Water for Injection, USP | N/A | To 1 mL | To 1 mL |

Example 3: Method of Manufacture

Compositions can be prepared by dissolving all of the excipients in water for injection (WFI) and filtering the solution into another pre-sterilized tank. To this solution, dispensed medroxyprogesterone acetate was added in small increments with continuous mixing. The compounded bulk suspension was steam sterilized in the tank in the temperature range of 122° C. to 125° C. for a minimum of 15 minutes and a F0 value≥12 minutes. After steam sterilization, the bulk was cooled to room temperature. Prior to final weight make up with water for injection through a sterile filter, the pH of the suspension was measured and adjusted if needed with 0.1 N HCl or 0.1 N NaOH (through pH filter). The compounded and sterilized bulk suspension was aseptically filled into pre-sterilized and depyrogenated USP Type 1 glass vials and capped with pre-sterilized 13 mm rubber stopper and 13 mm flip-off aluminum seal. The entire batch of finished drug product underwent manual visual inspection for defects and then was stored in quarantine area until released.

Example 4: Preparation of Medroxyprogesterone Acetate Compositions for Stability Testing In accordance with a typical embodiment of the present invention, the compounding of a lab bath comprises two steps—preparation of excipient solution, then suspending the API in it. Final drug product was filled into vials and terminal sterilized.

500 g of WFI was added and heated to (35-40° C.) into 2 L compounding container. Docusate sodium was added and dissolved. Then the solution was cooled to room temperature or 20±5° C. followed by the addition and complete dissolution of polyethylene glycol, sodium sulfate, monosodium phosphate, di-basic sodium phosphate and methionine at 250 rpm. The drug substance was added uniformly to the excipient solution for over minimum of 30 minutes at 600 rpm with paddle stirrer and continued mixing for minimum of 30 minutes. Final volume was made up with water for injection. The paddle mixer was replaced with Silverson L5M-A homogenizer and the bulk suspension was homogenized for 30 min at 5000 rpm. Then the homogenizer speed was reduced to 600 rpm and the suspension was mixed for 14-18 hours.

The drug product was filled into vials and exposed to different storage conditions, including variations in temperature, and relative humidity, for up to 60 months. Vials were stored in both upright and inverted positions. The vials were tested during the course of the storage period for, e.g., bacterial endotoxins, closure integrity, physical appearance, impurity/degradation products, pH, assay, particle size, and viscosity.

Assessing the physical appearance and description of the product comprised providing (1) a description of the product, (2) assessing container closure integrity, and (3) assessing resuspendability.

Suitable test specimens matched the following description: white particles in suspension and free from visible extraneous contamination.

Container closure integrity was assessed by examining the test specimen and recording any observations. Suitable test specimens should match the following description: glass vial, aluminum seal, and no visible leak or other abnormalities.

Resuspendability was assessed by dispersing the product by shaking for a period of time and comparing to the description of the product. If the appearance matches the description with no signs of caking or agglomerated particles, it is suitable for use. Shaking time for achieving product description was noted.

Obtaining an "assay" of the product comprised calculating the amount of medroxyprogesterone acetate in the composition as a percent of the label claim 400 mg/ml) following the HPLC protocol detailed in Example 5.

An assessment of impurity/degradation products was obtained by following the HPLC protocol described in Example 7.

Particle size density, or PSD, was calculated by following the protocol described in Example 8.

Viscosity was calculated by following the protocol described in Example 9.

Results are summarized in Table 3. Each sample tested for syringeability. Syringeability was determined by withdrawing the composition using a common syringe and needle type (23 gauge, ⅜ inch safety needle) used for the administration of the pharmaceutically acceptable composition, dispensing the solution, and repeating five consecutive times. Each sample was confirmed to be syringeable. Five pumps of the syringe produced no clogging within the syringe or needle.

TABLE 3

| Time (Position)[1] | Temp (° C.) | Rel. Humidity | Dx(10) | Dx(50) | Dx(90) | pH | Impurities[3] | Assay[4] | Resuspend-ability[5] (seconds) |
|---|---|---|---|---|---|---|---|---|---|
| Initial | | | 3.03 | 9.22 | 20.23 | 6.72 | 0.17 | 103.63 | 35, 30 |
| 1 month (U) | 40 | 75 | 3.35 | 9.95 | 25.92 | 6.75 | 0.21 | 100.40 | 30, 60 |
| 1 month (U) | 60 | | 3.30 | 9.25 | 23.42 | 6.66 | 0.21 | 103.20 | 60, 90 |
| 2 month (U) | 40 | 75 | 3.02 | 9.34 | 21.57 | 6.73 | 0.19 | 100.15 | 30, 60 |
| 2 month (U) | 60 | | 3.24 | 9.54 | 20.60 | 6.23 | 0.18 | 98.45 | 45, 100 |
| 3 month (U) | 25 | 60 | 3.12 | 9.35 | 22.69 | 6.77 | 0.12 | 101.65 | 30, 30 |
| 3 month (I) | 25 | 60 | 3.22 | 9.57 | 22.69 | 6.74 | 0.12 | 101.25 | 30, 30 |
| 3 month (U) | 30 | 65 | 3.14 | 9.07 | 19.84 | 6.80 | 0.12 | 102.75 | 30, 30 |
| 3 month (U) | 40 | 75 | 3.14 | 8.83 | 18.74 | 6.72 | 0.11 | 102.55 | 30, 30 |
| 3 month (U) | 60 | | 3.32 | 9.18 | 21.40 | 6.06 | 0.12 | 101.80 | 30, 30 |
| 6 month (U) | 25 | 60 | 3.03 | 9.04 | 18.91 | 6.67 | 0.10 | 101.40 | 30, 30 |
| 6 month (I) | 25 | 60 | 3.03 | 8.98 | 19.01 | 6.65 | 0.10 | 101.95 | 30, 30 |
| 6 month (U) | 30 | 65 | 3.06 | 8.82 | 18.30 | 6.62 | 0.10 | 102.40 | 30, 30 |
| 6 month (U) | 40 | 75 | 3.05 | 8.93 | 19.42 | 6.58 | 0.10 | 102.35 | 30, 30 |

[1] U-upright, I-Inverted
[2] Dx(N) refers to the mathematical function wherein N represents the average particle diameter by mass. For example, Dx(10) is the diameter at which 10% of the sample's mass is comprised of particles with a diameter less than this value. Dx(50) is the diameter at which 50% of the sample's mass is comprised of particles with a diameter less than this value. Dx(90) is the diameter at which 90% of the sample's mass is comprised of particles with a diameter less than this value.
[3] Impurities are reported as a percentage of total specified/unspecified impurities.
[4] Assay refers to the percent of medroxyprogesterone acetate in the composition as a percent of the label claim, where the label claim is 400 mg/ml.
[5] Resuspendability is reported as the number of seconds of shaking prior to comparing to the description of the product where the test is performed in duplicate.

Example 5: HPLC Protocol for Calculating the Amount of Medroxyprogesterone Acetate in the Composition Equipment: Suitable UPLC pump capable of pumping at approximately 0.4 mL/minute; suitable UV-wavelength spectrophotometric detector or photodiode array (PDA) detector; Waters Acquity UPLC BEH C18, 2.1-mm (i.d.)× 100-mm, 1.7-µm particle size; suitable injection system; suitable data acquisition system; and suitable column oven.

Reagents: Acetonitrile, HPLC grade; formic acid, HPLC grade; and water, grade suitable for chromatographic analysis.

Chromatographic parameters are as follows:

TABLE 4

| Chromatographic parameters | |
|---|---|
| Flow Rate | 0.4 mL/minute |
| Detector | 245 nm (PDA: 190-400 nm, for ID only) |
| Injection Volume | 2.0 µL |
| Column Set Temperature | 55° C. |
| Run Time | 20.0 min |
| Needle Wash | Diluent |
| Initial Pressure | 6000-8000 psi |

The parameters may be adjusted to achieve the proper chromatography: flow rate, detector sensitivity, mobile phase proportions (not composition), column dimensions and particle size. The gradient table is as follows:

TABLE 5

| Gradient table | | |
|---|---|---|
| Time (min) | Mobile Phase A (%) | Mobile Phase B (%) |
| 0.0 | 57.0 | 43.0 |
| 11.0 | 57.0 | 43.0 |
| 11.5 | 5.0 | 95.0 |
| 14.5 | 5.0 | 95.0 |
| 15.0 | 57.0 | 43.0 |
| 20.0 | 57.0 | 43.0 |

Preparation of the mobile phase A is achieved by adding 1 mL of formic acid to 1000 mL of water in a suitable container and mixing well then filtering the solution through a 0.2-µm nylon membrane filter, mixing well and labeling.

Preparation of the mobile phase B is achieved by using acetonitrile, filtering through a 0.2-µm nylon membrane filter, mixing well and labeling.

Preparation of the diluent is achieved by combining 500 mL of water and 500 mL of acetonitrile, mixing well, filtering through a 0.2-µm nylon membrane filter, mixing well and labeling.

Preparation of the standard solution is achieved by weighing accurately about 50 mg of medroxyprogesterone acetate reference standard into a 100-mL volumetric flask, adding approximately 90 mL of Diluent, mixing and sonicating to dissolve if necessary, allowing to cool to room temperature, diluting to volume with Diluent, mixing well and labeling.

Preparation of the resolution solution is achieved by weighing approximately 5.0 mg of medroxyprogesterone acetate for system suitability CRS into a 10-mL volumetric flask, adding approximately 7.5 mL of diluent, mixing and sonicating to dissolve if necessary, diluting to volume with diluent, mixing well and labeling.

Preparation of the sample solution is achieved by weighing the drug product vial with cap to obtain the initial weight. The next step is resuspending the product by vigorously shaking the vial for not less than 20 seconds before use and transferring the content in the vial to a volumetric flask as indicated below. The next step is rinsing the vial with Diluent and making sure no suspension is remaining in the vial and on the cap. The next step is making appropriate dilutions with diluent to reach a final sample concentration of 0.4 to 0.6 mg/mL, sonicating if necessary to dissolve all solids during dilution, allowing cooling to room temperature after sonication, drying the empty vial and cap, and weighing the empty vial with cap to obtain the final weight.

Those of skill in the art will readily appreciate that weights and volumes described herein may be adjusted, so long as the initial and final concentrations are the same.

To obtain the chromatograph, the diluent is injected, and then the resolution solution and standard solution are injected, and peak areas are recorded. Once the system suitability requirements have been met, the standard and sample solutions are injected following current procedures. Finally, the amount of medroxyprogesterone acetate is calculated using standard algorithms known to those in the art.

Example 6: HPLC Protocol for Determining Composition Dissolution

Equipment: Suitable UPLC pump capable of pumping at approximately 0.4 mL/minute; Waters Acquity UPLC BEH C18, 2.1-mm (i.d.)×100-mm, 1.7-μm particle size; suitable injection system; suitable UV-wavelength detector or photodiode assay (PDA) detector; suitable data acquisition system; and suitable column oven.

Reagents: Acetonitrile, HPLC grade; formic acid, Sodium Dodecylsulfate; and water, grade suitable for chromatographic analysis.

Chromatographic parameters are as follows:

TABLE 6

| Chromatographic parameters | |
|---|---|
| Flow Rate | 0.4 mL/minute |
| Detector | 245 nm (PDA: 190-400 nm, for ID only) |
| Injection Volume | 2.0 μL |
| Column Set Temperature | 55° C. |
| Run Time | About 5 minutes |
| Needle Wash | Diluent |

The dissolution parameters are as follows:

TABLE 7

| Dissolution parameters | |
|---|---|
| Apparatus | USP Apparatus 2 (paddles) |
| Rotation Speed | 50 rpm |
| Dissolution Medium | 0.5% SDS in water |
| Volume | 900 mL |
| Temperature | 37 ± 0.5° C. |
| Distance from bottom | 2.5 cm |
| Time points | 30 min |

Preparation of the mobile phase is achieved by combining 1000 mL of water and 1000 mL of acetonitrile, mixing well, filtering through a 0.2-μm nylon membrane filter, mixing well and labeling.

Preparation of the dissolution medium is achieved by weighing about 30 g of SDS, transferring the SDS into a 6 L flask, adding approximately 5 L of water, stirring until dissolved, diluting to 6 L with water, mixing well and labeling. The dissolution medium is used as the diluent.

Preparation of the standard solution is achieved by weighing accurately about 22 mg of medroxyprogesterone acetate reference standard into a 100-mL volumetric flask, adding approximately 5 mL of diluent, mixing and sonicating to dissolve if necessary, allowing to cool to room temperature, diluting to volume with diluent, mixing well and labeling. Those of skill skill in the art will readily appreciate that weights and volumes can be adjusted, provided the concentration of the standard solution is the same.

Preparation of the sample solution is achieved by manually withdrawing an appropriate volume of the sample solution at each time point, centrifuging the sample solution at 3,000 rpm for about 5 minutes and using the supernatant for analysis.

To obtain the chromatograph, the diluent is injected, and then the resolution solution and standard solution are injected, and peak areas are recorded. Once the system suitability requirements have been met, the standard and sample solutions are injected following current procedures. Finally, the percent release is calculated using standard algorithms known to those in the art.

Example 7: HPLC Protocol for Determining the Amount of Impurities/Degradation Products Equipment: Suitable UPLC pump capable of pumping at approximately 0.4 mL/minute; suitable UV-wavelength spectrophotometric detector or photodiode array (PDA) detector; Waters Acquity UPLC BEH C18, 2.1-mm (i.d.)× 100-mm, 1.7-μm particle size; suitable injection system; suitable data acquisition system; and suitable column oven.

Reagents: Acetonitrile, HPLC grade; formic acid, HPLC grade; tetrahydrofuran (THF), HPLC grade; and water, grade suitable for chromatographic analysis.

Chromatographic parameters are as follows:

TABLE 8

| Chromotographic parameters | |
|---|---|
| Flow Rate | 0.4 mL/minute |
| Detector | 245 nm (PDA: 190-400 nm, for ID only) |
| Injection Volume | 5.0 μL |
| Column Set Temperature | 55° C. |
| Run Time | 30.0 min |
| Needle Wash | Diluent |
| Initial Pressure | 6000-8000 psi |

The parameters may be adjusted to achieve the proper chromatography: flow rate, detector sensitivity, mobile phase proportions (not composition), column dimensions and particle size. The gradient table is as follows:

TABLE 9

| Gradient table | | |
|---|---|---|
| Time (min) | Mobile Phase A (%) | Mobile Phase B (%) |
| 0.0 | 80.0 | 20.0 |
| 10.0 | 70.0 | 30.0 |
| 22.0 | 70.0 | 30.0 |
| 22.1 | 5.0 | 95.0 |
| 25.0 | 5.0 | 95.0 |

TABLE 9-continued

Gradient table

| Time (min) | Mobile Phase A (%) | Mobile Phase B (%) |
|---|---|---|
| 25.1 | 80.0 | 20.0 |
| 30.0 | 80.0 | 20.0 |

Preparation of the mobile phase A is achieved by adding 1 mL of formic acid to 1000 mL of water in a suitable container and mixing well then filtering the solution through a 0.2-μm nylon membrane filter, mixing well and labeling.

Preparation of the mobile phase B is achieved by combining acetonitrile and THF in a ratio of 65:35, filtering through a 0.2-μm nylon membrane filter, mixing well and labeling.

Preparation of the diluent is achieved by combining 500 mL of water and 500 mL of acetonitrile, mixing well, filtering through a 0.2-μm nylon membrane filter, mixing well and labeling.

Preparation of the stock standard solution is achieved by weighing accurately about 50 mg of medroxyprogesterone acetate reference standard into a 100-mL volumetric flask, adding approximately 90 mL of diluent, mixing and sonicating to dissolve if necessary, allowing to cool to room temperature, diluting to volume with diluent, mixing well and labeling.

Preparation of the standard solution is achieved by pipetting 1.0 mL of the stock standard solution into a 200-mL volumetric flask, diluting to volume with diluent, mixing well and labeling.

Preparation of the resolution solution is achieved by weighing approximately 5.0 mg of medroxyprogesterone acetate for system suitability CRS into a 10-mL volumetric flask, adding approximately 7.5 mL of diluent, mixing and sonicating to dissolve if necessary, diluting to volume with Diluent, mixing well and labeling.

Preparation of the quantitation limit solution is achieved by pipetting 5.0 mL of the standard solution into a 50-mL volumetric flask, diluting to volume with diluent, mixing well and labeling.

Preparation of the sample solution is achieved by weighing the drug product vial with cap to obtain the initial weight. The next step is resuspending the product by vigorously shaking the vial for not less than 20 seconds before use and transferring the content in the vial to a volumetric flask as indicated below. The next step is rinsing the vial with Diluent and making sure no suspension is remaining in the vial and on the cap. The next step is making appropriate dilutions with diluent to reach a final sample concentration of 0.4 to 0.6 mg/mL, sonicating if necessary to dissolve all solids during dilution, allowing cooling to room temperature after sonication, drying the empty vial and cap, and weighing the empty vial with cap to obtain the final weight.

Those of skill in the art will readily appreciate that weights and volumes described herein may be adjusted, so long as the initial and final concentrations are the same.

To obtain the chromatograph, the diluent is injected, and then the resolution solution and standard solution are injected, and peak areas are recorded. Once the system suitability requirements have been met, the standard and sample solutions are injected following current procedures. Finally, the amount of impurities/degradation products present in a sample is calculated using standard algorithms known to those in the art.

Example 8: Protocol for Measuring Particle Size in the Composition

Equipment: Malvern laser diffraction mastersizer 3000 or equivalent and measuring cell (HydroMV or equivalent).

Reagents: water, suitable for analytical analysis and polysorbate 80.

TABLE 10

| Parameters | |
|---|---|
| Particle RI | 1.536 (also for blue light) |
| Absorption | 0.01 (also for blue light) |
| Dispersant | 0.05% polysorbate 80 in water |
| Dispersant RI | 1.33 |
| Particle Shape | Non-spherical |
| Blue light | Enabled |
| Measuring time | 10 seconds |
| Background measuring time | 10 seconds |
| Measurements | 3 |
| Obscuration | 7-12% |
| Speed rate of the flow cell | 1500 rpm |
| Sonication | 30 seconds |
| Sonication power | 50% |
| Premeasurement delay | 10 seconds |
| Analysis model | General purpose |
| Result type | Volume distribution |

The dispersant is prepared by weighing about 2 g polysorbate 80 in a 200-mL volumetric flask, diluting to volume with water, mixing well and labeling as polysorbate 80 stock. The concentration of polysorbate 80 is 1%. Next, 10 mL of Polysorbate 80 Stock is pipetted into a 2000-mL volumetric flask, diluted to volume with water, mixed well and labeled. The concentration of polysorbate 80 is 0.005%.

The cell is cleaned before starting measurement and between runs with degassed water.

The background measurement is taken by filling the measuring cell with dispersant, starting recirculation, and starting the background measurements.

The sample measurement is taken by resuspending the sample dispersion by vigorously shaking for not longer than 20 seconds before use, using a suitable syringe and needle with gauge number 23 or lower to transfer the suspension. The next step is slowly adding drop wise to the measuring cell filled with dispersant, until an obscuration of 7-12% is reached, then starting sonication for 30 sec at power of 50%, allowing the sample to stir about 10 seconds at 1500 rpm, and starting the measurement. If the weighted residual is greater than 3%, repeat the experiment.

Example 9: Protocol for Measuring Viscosity

Equipment: Brookfield Viscometer DV-II+ PRO, or equivalent and cone spindle CPE-40, CPA-40Z or equivalent.

Reagents: Brookfield viscosity general purpose silicone fluid, 10 cP at 25° C.

Measurement conditions: volume of 0.5 mL, spindle speed of 12 rpm and temperature of 25° C.

To time the use performance check, the viscometer is auto zeroed, the spindle is selected and the electronic gap is set. With the viscometer stopped, the sample cup is removed and 0.5 mL of a 10 cP Brookfield viscosity standard is pipetted into the cup. The sample cup is connected to the viscometer and sufficient time is allowed for the temperature to reach equilibrium. A viscometer speed is selected and the spindle is rotated. The temperature, spindle speed and viscosity are recorded. The instrument and viscosity standard fluid error are combined to calculate the total allowable error using calculations known to one of skill in the art.

Other instrumentation, for example, an Anton Paar Rheometer, can also be used to measure viscosity, using techniques and methods known in the art.

Example 10: Local Tolerance Studies

Initial selection of medroxyprogesterone injectable suspension at 300 mg/mL with Polysorbate 80 and medroxyprogesterone acetate injectable suspension at 400 mg/mL was based on plasma exposure and tolerability data collected from an ongoing non-good laboratory practice (GLP) pharmacokinetic and tolerability study in New Zealand White (NZW) rabbits. In this study 6 groups of 5 female NZW rabbits received a single subcutaneous administration of MPA in different formulations into the scapular region. Group 1 animals received injection of Depo-SubQ Provera 104, the listed drug, and a second administration after 3 months, resulting in all animals receiving a total dose of 208 mg. Groups 2, 3, and 5 were terminated after 3 months and groups 1, 4, and 6 will be followed for 1 year.

Figure 2:
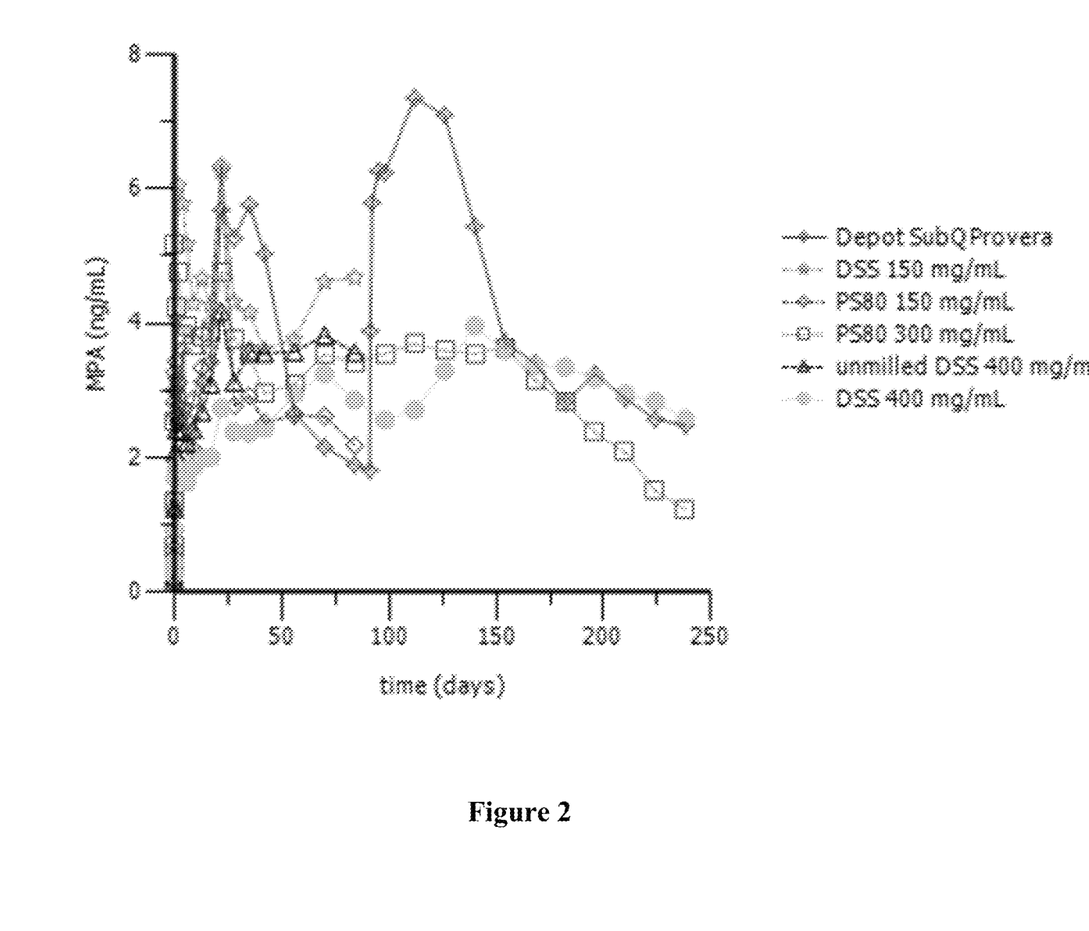
FIG. 2 depicts mean plasma concentration time profiles of medroxyprogesterone acetate in rabbits up to day 239 postdose.

A summary of the non-GLP exploratory rabbit pharmacokinetic study with data up to study day 239 is provided in Table 12.

postdose and were similar compared to the listed drug (FIG. 2). The 2-fold higher single dose of MPA in the test formulations (groups 2 to 6) did not result in higher plasma concentrations.

Upon gross tissue assessment of the injection site, only slight edema (grade 1) was noted 2 to 4 hours dose in 1 or 2 rabbits in all test formulation-treated groups; and no gross tissue abnormalities were noted on day 2 postdose and thereafter (up to day 29, when formal injection site scoring was discontinued). There were only minimal (non-statistically significant) differences noted in hematology and clinical pathology.

Based on this data and preliminary stability data, the safety of both medroxyprogesterone formulations was assessed as follows. The medroxyprogesterone acetate composition with DSS was evaluated in a 9-month GLP rabbit local tolerance study. Also evaluated in the study was a less stable medroxyprogesterone acetate composition at 300 mg/mL containing polysorbate 80. The two formulations were composed of different excipients and different concentrations of medroxyprogesterone acetate, but the overall dose was fixed by injecting a smaller volume for the claimed composition, which had the more concentrated MPA. A group of rabbits assigned to this trial received the referenced marketed comparator, Depo-SubQ Provera 104®.

The study design is summarized in Table 12, below.

TABLE 11

Non-GLP Exploratory Rabbit Pharmacokinetic Study

| Group No. | Formulation | Dose route | Target dose volume (mL/animal) | Target dose level (mg/animal/dose) | Nominal conc. (mg/mL) | Mean MPA average plasma conc. (ng/mL) |
|---|---|---|---|---|---|---|
| 1 | Depo-SubQ Provera 104® | Sc | 0.65 | 104 | 160 | 4.13 (22.0) |
| 2 | Medroxyprogesterone in docusate sodium | Sc | 1.39 | 208 | 150 | 4.41 (13.4) |
| 3 | Medroxyprogesterone in polysorbate 80 | Sc | 1.39 | 208 | 150 | 2.99 (18.2) |
| 4 | Medroxyprogesterone in polysorbate 80 | Sc | 0.69 | 208 | 300 | 3.15 (8.9) |
| 5 | Unmilled medroxyprogesterone in docusate sodium | Sc | 0.52 | 208 | 400 | 3.39 (37.8) |
| 6 | Medroxyprogesterone in docusate sodium | Sc | 0.52 | 208 | 400 | 2.93 (39.9) |

Figure 1:
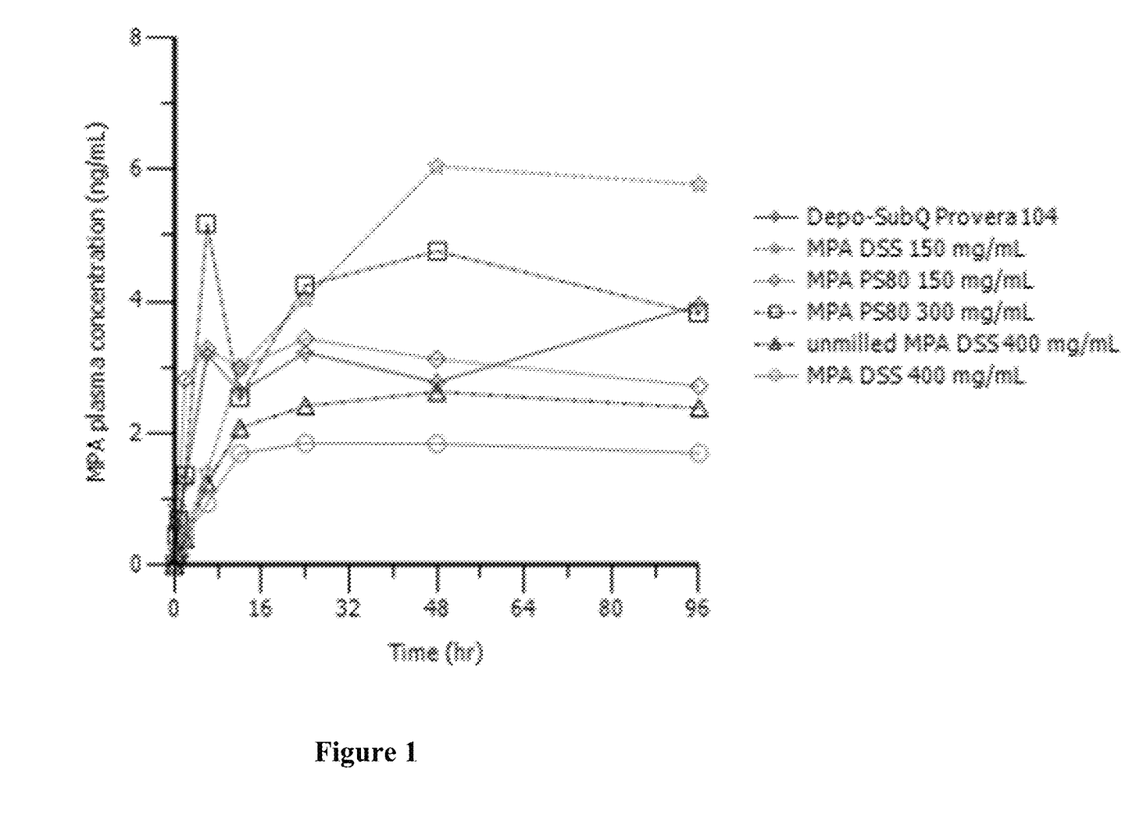
FIG. 1 depicts mean plasma concentration time profiles of medroxyprogesterone acetate in rabbits up to 96 hours postdose.

Preliminary results obtained from the non-GLP pharmacokinetic study in NZW rabbits did not display a significant burst-effect in rabbits (FIG. 1). Generally, mean steady-state MPA plasma levels were reached within 12 to 24 hours

TABLE 12

Experimental design of a 9-month GLP local tolerance investigation in female rabbits

| Group No. | Test material | Dose level (mg) | Dose concentration (mg/mL) | Dose volume (mL) | No. of females assigned |
|---|---|---|---|---|---|
| 1 | 0.9% Sodium chloride for injection | 0 | 0 | 1 | 12 |
| 2 | Depo-SubQ Provera 104 ® | 104 | 160 | 0.65 | 12 |
| 3 | Placebo of medroxyprogesterone acetate injectable suspension, 300 mg/mL with 3.0 mg/mL of polysorbate 80 | 0 | 0 | 1 | 12 |
| 4 | Medroxyprogesterone acetate injectable suspension, 300 mg/mL with 3.0 mg/mL of polysorbate 80 | 300 | 300 | 1 | 12 |

TABLE 12-continued

Experimental design of a 9-month GLP local tolerance investigation in female rabbits

| Group No. | Test material | Dose level (mg) | Dose concentration (mg/mL) | Dose volume (mL) | No. of females assigned |
|---|---|---|---|---|---|
| 5 | Placebo of medroxyprogesterone acetate injection suspension, 400 mg/mL with DSS at 1.5 mg/mL | 0 | 0 | 0.75 | 12 |
| 6 | Medroxyprogesterone acetate injection suspension, 400 mg/mL with DSS at 1.5 mg/mL | 300 | 400 | 0.75 | 12 |

The listed drug (group 2) was subcutaneously dosed on day 1, and a second dose of the listed drug occurred on day 90, while groups receiving saline control, vehicle control, or experimental formulations were dosed just on day 1. The highest dose level administered in the study was 300 mg. Rabbits were assessed for signs of clinical abnormalities. In addition, at day 7 and month 3, rabbits were euthanized humanely, and the following tissues were microscopically assessed: injection site with associated regional draining lymph nodes (interscapular and axillary), liver, ovaries, uterus, adrenal glands, and any abnormal-appearing tissues. All other collected tissues were stored in fixative. The same necropsy/organ collection/microscopic assessment procedure occurs during months 6 and 9.

Full clinical pathology parameters (hematology, clinical biochemistry, coagulation panel, and urinalysis) were assessed and conventional microscopic pathology assessments to determine organ/tissue/cellular alterations are included. Furthermore, plasma toxicokinetics samples were collected at predose, and at 6, 24 (study day 2), and 48 (study day 3) hours postdose and on study day 7, 14, 30, 60, 90, 120, 150, 180, and 270 and assayed using a validated bioanalytical assay.

Observations made during the 7-day interim necropsy time point noted the aqueous (vehicle) component of both formulations to be completely absorbed from the site of injection and only a white, flat, solid cake-like substance (same color of MPA) remained at the site of injection. These observations concluded that the vehicle component of the DSS-containing formulation was acutely absorbed into systemic circulation. The study termination time points are provided in Table 13.

TABLE 13

Rabbit study termination time points

| Group No. | Test material | Dose level (mg) | Number of females required per interim and terminal euthanasia time point | | | |
|---|---|---|---|---|---|---|
| | | | 7-day | 3-mo. | 6-mo. | 9-mo. |
| 1 | 0.9% Sodium chloride for injection | 0 | 3 | 3 | 3 | 3 |
| 2 | Depo-SubQ Provera 104 ® | 104 | 3 | 3 | 3 | 3 |
| 3 | Placebo of medroxyprogesterone acetate injectable suspension, 300 mg/mL with 3.0 mg/mL of polysorbate 80 | 0 | 3 | 3 | 3 | 3 |
| 4 | Medroxyprogesterone acetate injectable suspension, 300 mg/mL with 3.0 mg/mL of polysorbate 80 | 300 | 3 | 3 | 3 | 3 |
| 5 | Placebo of medroxyprogesterone acetate injection suspension, 400 mg/mL with DSS at 1.5 mg/mL | 0 | 3 | 3 | 3 | 3 |
| 6 | Medroxyprogesterone acetate injection suspension, 400 mg/mL with DSS at 1.5 mg/mL | 300 | 400 | 0.75 | 12 | |

Example 11: Medroxyprogesterone Acetate Compositions

The quantitative composition and function of each component in an exemplary embodiment of the disclosure is provided in Table 14.

TABLE 24

Unit composition in medroxyprogesterone acetate compositions

| Ingredients | Function of Components | Concentration (mg/mL) | Content (mg/vial) |
|---|---|---|---|
| Medroxyprogesterone Acetate, USP | Active Pharmaceutical Ingredient | 200 | 252 |
| Polyethylene glycol 3350 NF | Suspending Agent | 20.3 | 25.58 |
| Docusate sodium, USP | Surfactant | 1.5 | 1.89 |
| Sodium sulfate anhydrous, USP | Tonicity Adjuster | 11 | 13.86 |
| L-Methionine, USP | Stabilizer | 1.5 | 1.89 |
| Monobasic sodium phosphate, Anhydrous, USP | Buffer | 0.25 | 0.32 |
| Dibasic Sodium phosphate Anhydrous, USP | Buffer | 0.52 | 0.66 |
| Water for Injection, USP | Vehicle | Q.S to 1 mL | Q.S to 1.26 mL |

Example 12: Medroxyprogesterone Acetate Compositions

The quantitative composition and function of each component in an exemplary embodiment of the disclosure is provided in Table 15.

TABLE 35

Unit composition in medroxyprogesterone acetate compositions

| Ingredients | Function of Components | Concentration (mg/mL) | Content (mg/vial) |
|---|---|---|---|
| Medroxyprogesterone Acetate, USP | Active Pharmaceutical Ingredient | 150 | 189 |
| Polyethylene glycol 3350 NF | Suspending Agent | 20.3 | 25.58 |
| Docusate sodium, USP | Surfactant | 1.5 | 1.89 |
| Sodium sulfate anhydrous, USP | Tonicity Adjuster | 11 | 13.86 |
| L-Methionine, USP | Stabilizer | 1.5 | 1.89 |
| Monobasic sodium phosphate, Anhydrous, USP | Buffer | 0.25 | 0.32 |
| Dibasic Sodium phosphate Anhydrous, USP | Buffer | 0.52 | 0.66 |
| Water for Injection, USP | Vehicle | Q.S to 1 mL | Q.S to 1.26 mL |

Example 13: Medroxyprogesterone Acetate Compositions

The quantitative composition and function of each component in an exemplary embodiment of the disclosure is provided in Table 16.

TABLE 46

Unit composition in medroxyprogesterone acetate compositions

| Ingredients | Function of Components | Concentration (mg/mL) | Content (mg/vial) |
|---|---|---|---|
| Medroxyprogesterone Acetate, USP | Active Pharmaceutical Ingredient | 200 | 252 |
| Polyethylene glycol 3350 NF | Suspending Agent | 10.15 | 12.789 |
| Docusate sodium, USP | Surfactant | 0.75 | 0.945 |
| Sodium chloride | Tonicity Adjuster | 4.5 | 5.67 |
| Sodium sulfate anhydrous, USP | Tonicity Adjuster | 5.5 | 6.93 |
| L-Methionine, USP | Stabilizer | 0.75 | 0.945 |
| Monobasic sodium phosphate, Anhydrous, USP | Buffer | 0.125 | 0.1575 |
| Dibasic Sodium phosphate Anhydrous, USP | Buffer | 0.26 | 0.3276 |
| Water for Injection, USP | Vehicle | Q.S to 1 mL | Q.S to 1.26 mL |

Example 14: Alternative Sterilization Procedure

Compositions can be prepared by dissolving all of the excipients in water for injection (WFI) and filtering the solution into another pre-sterilized tank. To this solution, dispensed medroxyprogesterone acetate is added in small increments with continuous mixing. Prior to final weight make up with water for injection through a sterile filter, the pH of the suspension is measured and adjusted if needed with 0.1 N HCl or 0.1 N NaOH (through pH filter). Previously prepared suspension is continuously mixed during filling into vials and/or syringes and/or cartridges. The filled units (vials/syringes/cartridges) are steam sterilized for a minimum of 15 minutes at 122° C. After steam sterilization, the filled units (vials/syringes/cartridges) are cooled to room temperature. The entire batch of finished drug product undergoes manual visual inspection for defects and then is stored in quarantine area until released.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. More specifically, it will be apparent that certain solvents which are both chemically and physiologically related to the solvents disclosed herein may be substituted for the solvents described herein while the same or similar results would be achieved. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for preventing pregnancy or for treating endometriosis-associated pain, renal carcinoma, or endometrial carcinoma in a female patient comprising subcutaneously administering to the patient a composition comprising medroxyprogesterone acetate at a concentration of about 360 mg/ml to 440 mg/ml, docusate sodium at a concentration of about 1.35 mg/ml to 1.65 mg/ml, polyethylene glycol, and water.

2. The method according to claim 1, wherein the composition is administered once every four months.

3. The method according to claim 1, wherein the composition is administered once every five months.

4. The method according to claim 1, wherein the composition is administered once every six months.

5. The method according to claim 1, wherein the polyethylene glycol is at a concentration of about 18 mg/ml to 23 mg/ml.

6. The method according to claim 1, wherein the polyethylene glycol is polyethylene glycol 3350.

7. The method according to claim 1, wherein the composition further comprises a sulfate salt or a sodium salt.

8. The method according to claim 7, wherein the sulfate salt is sodium sulfate and the sodium salt is sodium chloride.

9. The method according to claim 1, wherein the composition further comprises a stabilizer.

10. The method according to claim 9, wherein the stabilizer is methionine.

11. The method according to claim 9, wherein the stabilizer is thioglycerol, monothioglycerol, lipoic acid, propyl gallate, cysteine, sodium formaldehyde sulfoxylate, or dihydrolipoic acid.

12. The method according to claim 1, wherein the composition further comprises a buffering salt.

13. The method according to claim 12, wherein the buffering salt is a phosphate salt or a combination of phosphate salts.

14. The method according to claim 13, wherein the buffering salt is monobasic sodium phosphate, dibasic sodium phosphate, or a combination thereof.

15. The method according to claim 1, wherein the composition is in a form of a single unit dose.

16. The method according to claim 1, wherein the composition has a pH of about 4.0 to about 7.0.

17. The method according to claim 1, wherein the composition has a pH of 6.6 to 6.7.

18. The method according to claim 1, wherein the composition comprises sodium sulfate, methionine, monobasic sodium phosphate, and dibasic sodium phosphate.

19. The method according to claim 1, wherein the composition is in the form of an aqueous suspension.

20. The method according to claim 1, wherein the composition is for extended release up to 6 months, comprising medroxyprogesterone acetate at a concentration of about 360 mg/ml to 440 mg/ml, docusate sodium at a concentration of about 1.35 mg/ml to 1.65 mg/ml, polyethylene glycol 3350 at a concentration of about 18 mg/ml to 23 mg/ml, sodium sulphate, and methionine in an aqueous suspension.

* * * * *